United States Patent [19]
Mertens et al.

[11] Patent Number: 5,241,181
[45] Date of Patent: Aug. 31, 1993

[54] COINCIDENCE DETECTOR FOR A PET SCANNER

[75] Inventors: John D. Mertens, Oconomowoc; William L. Bhend, Birchwood, both of Wis.

[73] Assignee: General Electric Company, Milwaukee, Wis.

[21] Appl. No.: 919,456

[22] Filed: Jul. 27, 1992

[51] Int. Cl.$^5$ ............................................. G01T 1/172
[52] U.S. Cl. ................................ 250/363.03; 250/369
[58] Field of Search ........................... 250/363.03, 369

[56] References Cited

U.S. PATENT DOCUMENTS 4,284,890 8/1981 Thompson ..................... 250/363.03
4,983,841 1/1991 Stewart et al. ................... 250/358.1

OTHER PUBLICATIONS

A Real Time Digital Coincidence Processor For Positron Emission Tomography, H. M. Dent, et al., IEEE Transactions on Nuclear Science, vol. 33, No. 1, Feb. 1986.

Coincidence Detection and Selection in Positron Emissions Tomography Using VLSI, D. F. Newport, et al., IEEE Transactions on Nuclear Science, vol. 36, No. 1, Feb. 1989.

Primary Examiner—Constantine Hannaher
Attorney, Agent, or Firm—Quarles & Brady

[57] ABSTRACT

A PET scanner includes a coincidence detector circuit which compares time markers produced by a ring of detector modules. Detector module outputs are sampled every 250 nanoseconds and assembled into event data packets which are time multiplexed through the coincidence detector circuit. The coincidence detector circuit is formed around a set of ASICs which perform the comparisons necessary to detect coincidence events. Coincidence event data packets are sorted into sinograms and used to reconstruct images.

14 Claims, 5 Drawing Sheets

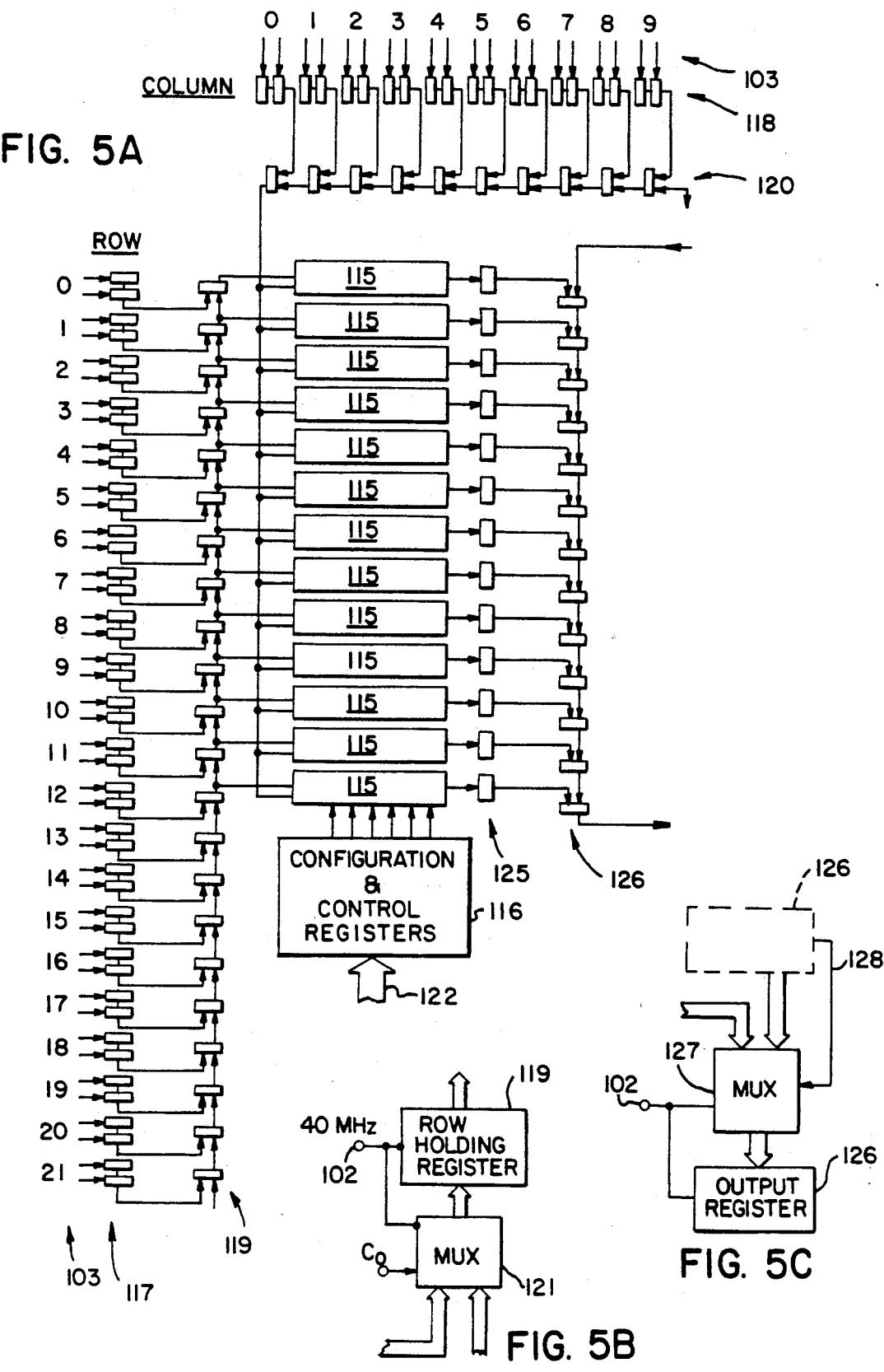

COINCIDENCE DETECTOR FOR A PET SCANNER

BACKGROUND OF THE INVENTION

The field of the invention is positron emission tomography (PET) scanners, and particularly circuits for detecting annihilation events by sensing the coincident receipt of gamma rays by a ring of detector crystals.

Positrons are positively charged electrons which are emitted by radionuclides that have been prepared using a cyclotron or other device. The radionuclides most often employed in diagnostic imaging are fluorine-18 ($^{18}$F), carbon-11 ($^{11}$C), nitrogen-13 ($^{13}$N), and oxygen-15 ($^{15}$O). These are employed as radioactive tracers called "radiopharmaceuticals" by incorporating them into substances, such as glucose or carbon dioxide. The radiopharmaceuticals are injected in the patient and become involved in such processes as blood flow, fatty acid and glucose metabolism, and protein synthesis.

As the radionuclides decay, they emit positrons. The positrons travel a very short distance before they encounter an electron, and when this occurs, they are annihilated and converted into two photons, or gamma rays. This annihilation event is characterized by two features which are pertinent to PET scanners—each gamma ray has an energy of 511 keV and the two gamma rays are directed in nearly opposite directions. An image is created by determining the number of such annihilation events at each location within the scanner's field of view.

The PET scanner includes one or more rings of detectors which encircle the patient and which convert the energy of each 511 keV photon into a flash of light that is sensed by a photomultiplier tube (PMT). Coincidence detection circuits connect to the detectors and record only those photons which are detected simultaneously by two detectors located on opposite sides of the patient. The number of such simultaneous events indicates the number of positron annihilations that occurred along a line joining the two opposing detectors. Within a few minutes hundreds of millions of events are recorded to indicate the number of annihilations along lines joining pairs of detectors in the ring. These numbers are employed to reconstruct an image using well known computed tomography techniques.

To produce an image it is necessary to provide a number of gamma ray detectors in a ring which surrounds the patient. If events are detected within a small time window by two detectors located on opposite sides of the ring, then a coincident event is recorded. Coincidence detection circuits are connected to each of the detectors in the ring and they look for such coincident events in all of the possible detector pair combinations. For example, in prior systems such as that described by D. F. Newport et al. in "Coincidence Detection and Selection in Positron Emission Tomography Using VLSI", *IEEE Transactions on Nuclear Science*, Vol. 36, No. 1, February 1989 the detector ring includes sixteen separate detector modules, and fifty-six separate module pairs are continuously monitored for coincidence events by the coincidence detector circuit. The coincidence detector circuit, therefore, has one complete channel for each possible detector pair to be examined, and these examinations are performed in parallel once each 256 nanosecond sample period. Even if multiple coincidence events occur during a given sample period, only one is recorded by such prior detector circuits.

To increase image resolution and reduce scanner deadtime, the number of detector modules must be increased. In the preferred embodiment of the present invention, for example, fifty-six separate detector modules are provided in the ring. To detect coincidence events for such a system using prior techniques would require 700 separate channels. Such a coincidence detector circuit is too complex and costly even when VLSI circuit technology is employed.

SUMMARY OF THE INVENTION

The present invention is a coincidence detector circuit for a PET scanner in which the total number of detector event pairs to be tested is divided into a plurality of sets of event pairs and the respective sets of event pairs are sequentially processed during each sample period. More specifically, the coincidence detector circuit includes a comparator circuit for receiving pairs of event data packets from respective detector modules and comparing time markers therein to determine if a coincidence event is present; shift means for changing the pair of event data packets applied to the comparator circuit such that a plurality of pairs of event data packets are compared during each sample period; and an output register for storing the location of the detector modules being compared and an indication of whether coincidence was determined.

A general object of the invention is to reduce the amount of circuitry needed to detect coincidence events without sacrificing performance. The sample period is divided into time increments and each channel of the coincidence detector circuit performs a comparison during each time increment. As a result, each channel can process a plurality of detector pair comparisons during each sample period and the total number of separate channels is reduced by a corresponding factor.

Another object of the invention is to detect and process all coincidence events which occur in an event period. Because each detector module spans a large axial field of view, it is very likely that multiple coincidence events will occur from the many imaging planes along the entire axial field of view. Prior systems cannot process multiple coincidence events in the same event period, and hence tended to limit the axial view of the system to only direct and cross slices.

Another object of the invention is to provide a coincidence detector circuit in which the transaxial field of view and the axial acceptance angle are configurable. Configuration data may be downloaded to the coincidence detector circuit and used in the comparison means to define the detectable coincidence event.

Another object of the invention is to provide a coincidence detector circuit in which the time window which defines a coincidence event is configurable.

Yet another object of the invention is to provide a coincidence detector that produces timing information when the PET scanner is operated in a calibration mode. The coincidence detector circuit outputs a time difference number in each coincidence data packet which may be employed to calibrate the scanner.

Yet another more specific object of the invention is to classify coincidence events. A tag bit is available in each coincidence data packet and it can be used to pass on information from the acquisition circuits concerning event conditions. For example, the tag bit may be employed to indicate whether the detected gamma rays have an energy level above a preset amount.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIGS. 5A-C are circuit diagrams of the coincidence circuit which forms part of the detector circuit of FIG. 4;

DESCRIPTION OF THE PREFERRED EMBODIMENT

Figure 1:
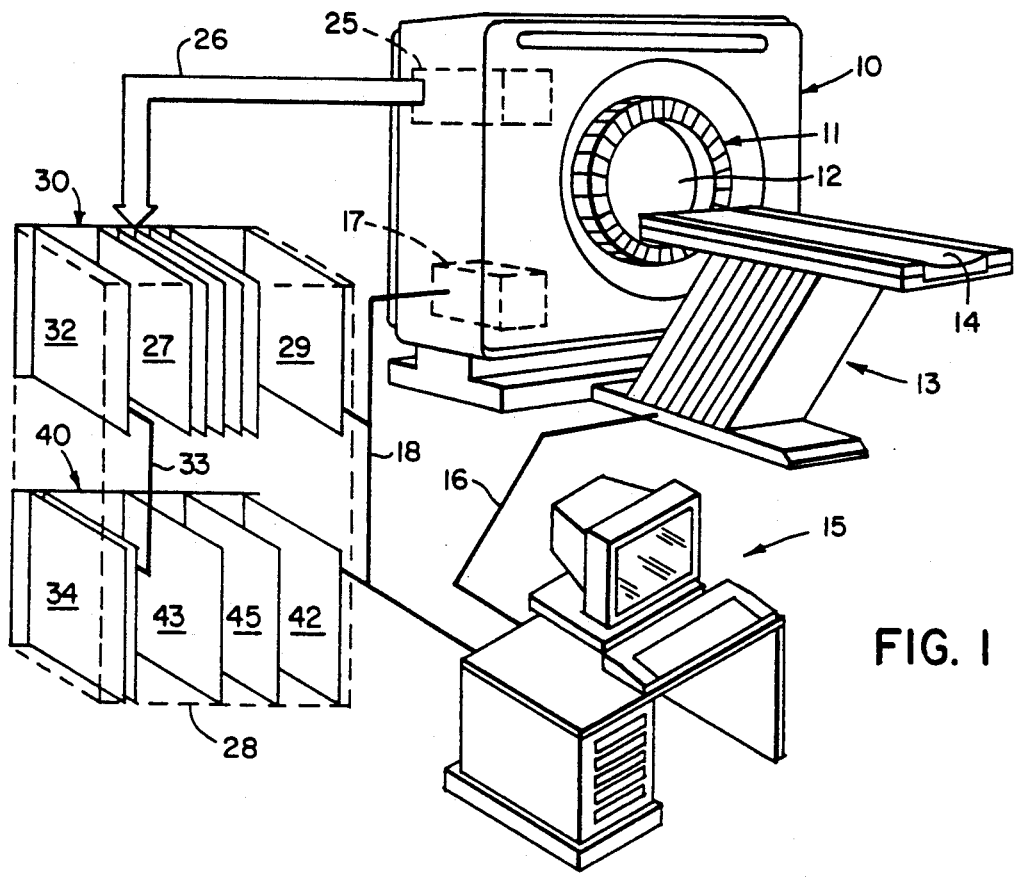
FIG. 1 is a pictorial view with parts cut away of a PET scanner system which employs the present invention.

Referring particularly to FIG. 1, the PET scanner system includes a gantry 10 which supports a detector ring assembly 11 about a central axis, or bore 12. A patient table 13 is positioned in front of the gantry 10 and is aligned with the central axis of the bore 12. A patient table controller (not shown) moves the table bed 14 into the bore 12 in response to commands received from an operator work station 15 through a serial communications link 16. A gantry controller 17 is mounted within the gantry 10 and is responsive to commands received from the operator work station 15 through a second serial communication link 18 to operate the gantry 10. For example, the gantry 10 can be tilted away from vertical on command from the operator, it can perform a "transmission scan" with a calibrated radionuclide source to acquire attenuation measurements, or it can perform a normal scan in which positron annihilation events are counted and an image is reconstructed.

Figure 2:
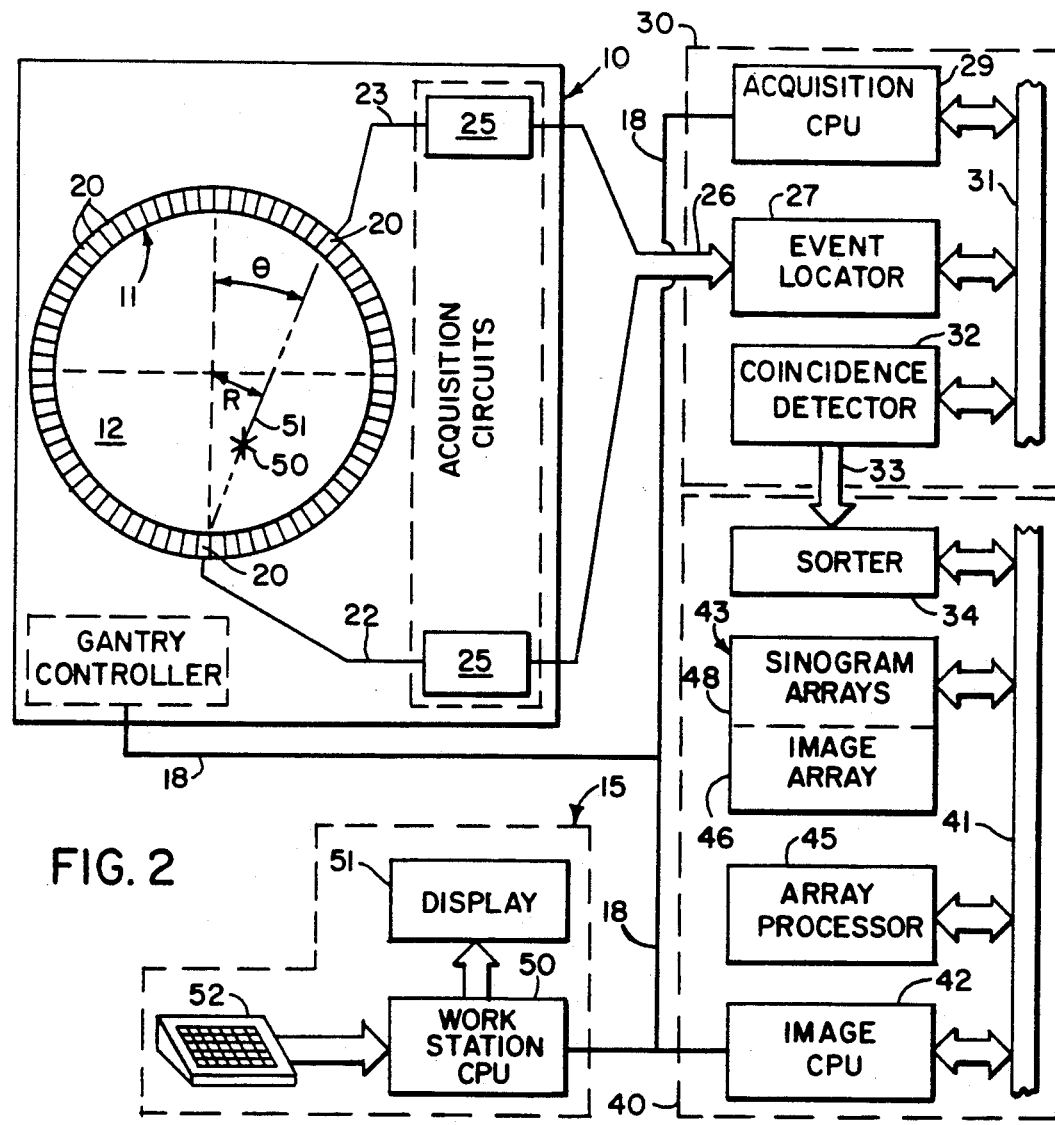
FIG. 2 is a schematic diagram of the PET scanner system of FIG. 1.
Figure 3:
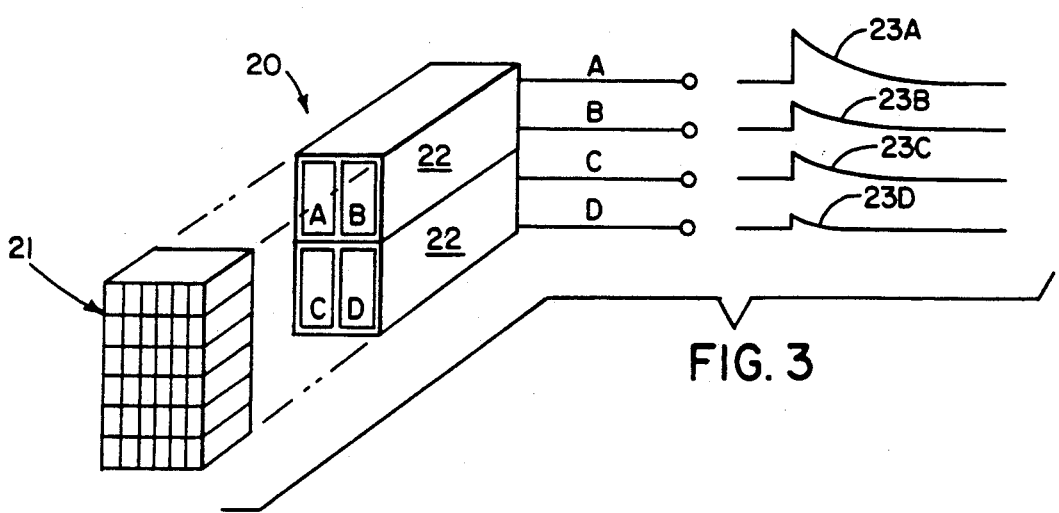
FIG. 3 is a pictorial view of a detector module which forms part of the PET scanner system of FIG. 1.

As shown best in FIGS. 2 and 3, the detector ring 11 is comprised of 56 detector modules, each module containing 6 detector blocks 20. Each block 20 includes a set of thirty-six bismuth germinate scintillator crystals 21 (abbreviated BGO) arranged in a 6×6 matrix and disposed in front of four photomultiplier tubes 22 (abbreviated PMT). Each PMT 22 produces an analog signal 23A-23D, which rises sharply when a scintillation event occurs, and then tails off exponentially with a time constant of 300 nanoseconds. The relative magnitudes of the analog signals 23A-23D is determined by the position in the 6×6 BGO matrix at which the scintillation event took place. The total magnitude of these signals is determined by the energy of the gamma ray which caused the scintillation event.

A set of acquisition circuits 25 are mounted within the gantry 10 to receive the four signals 23A-23D from each of the modules 20 in the detector ring 11. The acquisition circuits 25 determine the event coordinates within the block of BGO crystals 21 by comparing the relative signal strengths as follows:

$$x = (A+C)/(A+B+C+D); \quad (1)$$

$$z = (A+B)/(A+B+C+D). \quad (2)$$

These coordinates (x,z), along with the sum of all four signals (A+B+C+D) are then digitized and sent through a cable 26 to an event locater circuit 27 housed in a separate cabinet 28. Each acquisition circuit 25 also produces an event detection pulse (EDP) which indicates the exact moment the scintillation event took place.

Referring particularly to FIGS. 1 and 2, the event locater circuits 27 form part of a data acquisition processor 30 which periodically samples the signals produced by the acquisition circuits 25. The processor 30 has a backplane bus structure 31 which conforms with the VME standard, and an acquisition CPU 29 which controls communications on this bus 31 and links the processor 30 to the local area network 18. The event locator 27 is comprised of a set of separate circuit boards which each connect to the cable 26 and receive signals from corresponding acquisition circuits 25 in the gantry 10. The event locator 27 synchronizes the event with the operation of the processor 30 by detecting the event pulse (EDP) produced by an acquisition circuit 25, and converting it into an 8-bit time marker which indicates when within the current 250 nanosecond sample period the scintillation event took place. Also, this circuit 27 discards any detected events if the total energy of the scintillation is outside the range of 511 keV±20%. During each 250 nanosecond sample period, the information from each of the fifty-six detector modules is assembled into a set of digital numbers that indicate precisely when an event took place and the position of the BGO crystal 21 which detected the event. This event data packet is conveyed as two serial data streams to a coincidence detector 32 which is also part of the data acquisition processor 30. The format of this event data packet is listed in Table A.

TABLE A

| | |
|---|---|
| serial line 1 | bits 0–7 = event time marker |
| | bit 8 = event present bit |
| | bit 9 = reserved |
| serial line 2 | bits 0–8 = event location |
| | bit 9 = reserved |

The coincidence detector 32 accepts the event data packets from the event locators 27 and determines if any two of them are in coincidence. Coincidence is determined by a number of factors. First, the time markers in each event data packet must be within a preset time window of each other, and second, the locations indicated by the two event data packets must lie on a straight line which passes through the field of view (FOV) in the scanner bore 12. Events which cannot be paired are discarded, but coincident event pairs are located and recorded as a coincidence data packet that is conveyed through a serial link 33 to a sorter 34. Each coincidence data packet is a thirty-two bit data stream which includes a pair of digital numbers that precisely identify the location of the two BGO crystals 21 that detected the event. The format of the coincidence data packet is listed in Table B.

TABLE B

| Bit | Description |
|---|---|
| 0-4 | z position in crystal array |
| 5-8 | x position in crystal array |
| 9-14 | first detector module ring location |
| 15-19 | z position in crystal array |
| 20-23 | x position in crystal array |
| 24-29 | second detector module ring location |
| 30 | true/random event bit |
| 31 | reserved |

The sorter 34 is a circuit which forms part of an image reconstruction processor 40. The image reconstruction processor 40 is formed about a backplane bus 41 that conforms to the VME standard. An image CPU 42 controls the backplane bus 41 and it links the processor 40 to the local area network 18. A memory module 43 also connects to the backplane 41 and it stores the data used to reconstruct images. An array processor 45 also connects to the backplane 41 and it operates under the direction of the image CPU 42 to perform the image reconstruction using the data in memory module 43. The resulting image array 43 is stored in memory module 46 and is output by the image CPU 42 to the operator work station 15. The function of the sorter 34 is to receive the coincidence data packets and generate from them memory addresses for the efficient storage of the coincidence data. The set of all projection rays that point in the same direction ($\theta$) and pass through the scanner's field of view is a complete projection, or "view". The distance (R) between a particular projection ray and the center of the field of view locates that projection ray within the view. As shown in FIG. 2, for example, an event 50 occurs along a projection ray 51 which is located in a view at the projection angle $\theta$ and the distance R. The sorter 34 counts all of the events that occur on this projection ray (R,$\theta$) during the scan by sorting out the coincidence data packets that indicate an event at the two BGO detector crystals lying on this projection ray. The coincidence counts are organized in memory 43 as a set of two-dimensional arrays, one for each axial image plane, and each having as one of its dimensions the projection angle $\theta$ and the other dimension the distance R. This $\theta$ by R map of the measured events is called a histrogram, or more commonly the sinogram array 48.

Coincidence events occur at random and the sorter 34 quickly determines the $\theta$ and R values from the two crystal locations in each coincidence data packet and increments the count of the corresponding sinogram array element. The values of $\theta$ and R are calculated as follows:

$$\theta = (\phi_2 + \phi_1))/2 + 90°$$

$$R = r_0 \cos[(\phi_2 - \phi_1)/2]$$

where $\phi_1$ = angular orientation of first detector crystal;
$\phi_2$ = angular orientation of second detector crystal; and
$r_0$ = radius of detector ring. At the completion of the scan, the sinogram array 48 stores the total number of annihilation events which occurred along each ray R in each projection, or view $\theta$.

The array processor 45 reconstructs an image from the data in the sinogram array 48. First, however, a number of corrections are made to the acquired data to correct for measurement errors such as those caused by attenuation of the gamma rays by the patient, detector gain nonuniformities, random coincidences, and integrator deadtime. The corrected sinogram array is then Fourier transformed along both dimensions by the array processor 45 and multiplied by a two-dimensional filter array. The filtered data is then inverse Fourier transformed, and each array element is backprojected to form the image array 46. The image CPU 42 may either store the image array data on disk or tape (not shown) or output it to the operator work station 15.

The operator work station 15 includes a CPU 50, a CRT display 51 and a keyboard 52. The CPU 50 connects to the local area network 18 and it scans the keyboard 52 for input information. Through the keyboard 52 and associated control panel switches, the operator can control the calibration of the PET scanner, its configuration, and the positioning of the patient table for a scan. For example, the operator can enter configuration data through the keyboard 52 and download it to the coincidence detector 32 through the local area network 18 and the processor backplane 31. The operator can also control the display of the resulting image on the CRT display 51 and perform image enhancement functions using programs executed by the work station CPU 50.

Figure 4:
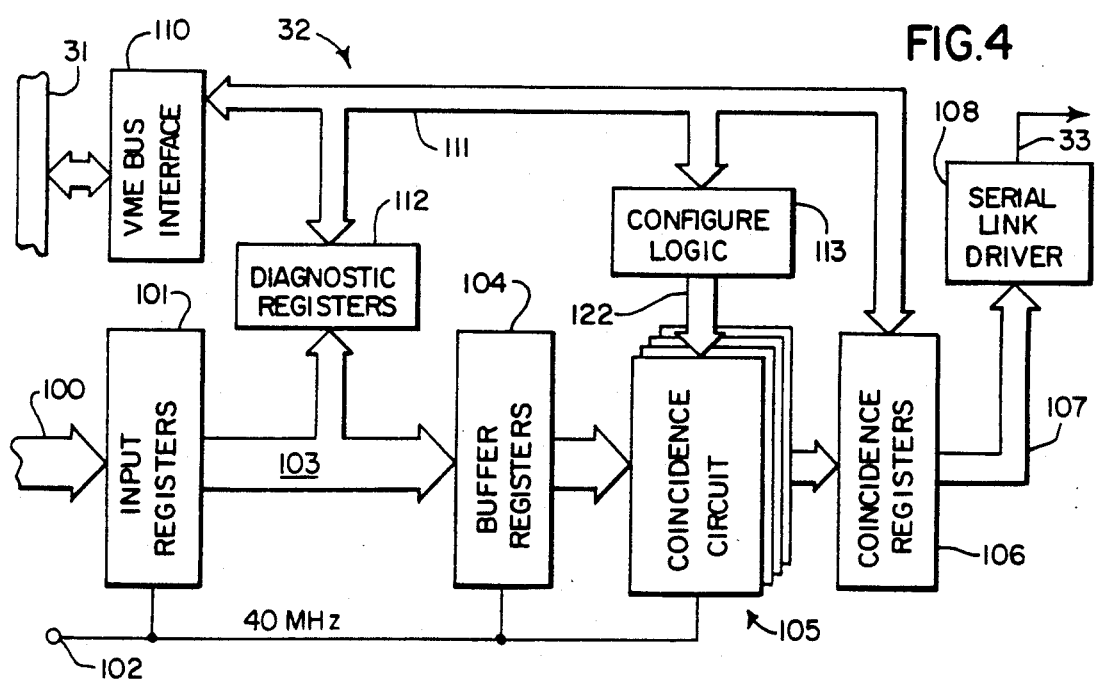
FIG. 4 is a block diagram of the preferred embodiment of the coincidence detector circuit employed in the PET scanner system of FIG. 2.

Referring particularly to FIG. 4, the coincidence detector circuit 32 of the present invention receives fifty-six pairs of serial data from the event locator 27 through a bus 100. Each bit in these serial bit streams is clocked into an input register 101 by a 40 MHz clock signal on line 102, is then transferred through a 112-lead bus 103 to corresponding buffer registers 104 on the next clock pulse, and is clocked into one (or more) of seven coincidence circuits 105 on the next clock pulse. During a 250 nanosecond sample period, therefore, the entire set of event data packets for the previous sample period is clocked into one of the coincidence circuits 105, and during the next 250 nanosecond sample period, this set of event data packets will be analyzed for coincidence events by the circuits 105. The resulting 32-bit coincidence data packets are output to coincidence registers 06 and are applied through a bus 107 to a fiber-optic serial link driver 108. The serial link driver 108 converts the 32-bit coincidence data packet to a serial bit stream which is conveyed through the fiber-optic link 33 to the sorter 34 as shown in FIG. 2.

Referring particularly to FIGS. 2 and 4, the coincidence detector circuit 32 is coupled to the backplane bus 31 by a VME bus interface circuit 110. This enables the acquisition CPU 29 to write data to elements of the coincidence detector circuit 32 through the backplane 31, or to read data therefrom. Such elements are connected to a module bus 111, and they include diagnostic registers 112 that connect to the bus 103 and intercept incoming event data packets, and the coincidence registers 106 that buffer the outgoing coincidence data packets. The connections to these registers 112 and 106 enable data to be monitored by diagnostic software and for test data to be inserted into the data stream by such software. And finally, the module bus 111 connects to a set of configure logic 113 which receives data that configures the operation of the coincidence circuits 105 as will be described in more detail below.

Each of the seven coincidence circuits 105 is an application specific integrated circuit ("ASIC") which employs VLSI technology. The ASICs 105 are identical and each includes ten pairs of serial inputs referred to herein as "column inputs" (0-9) and twenty-two pairs of serial inputs referred to herein as "row inputs" (0-21). The connections of each ASIC 105 to the fifty-six pairs of serial input data produced by the event locator 37 is indicated in Table C.

TABLE C

| ASIC # | COL # | ROW # | DET MODULE # |
|---|---|---|---|
| 1 | 0-9 | 0-21 | 0-9 |
|   |     |      | 16-37 |
| 2 | 0-9 | 0-20 | 0-9 |
|   |     |      | 29-49 |
| 3 | 0-9 | 0-21 | 10-19 |
|   |     |      | 26-47 |
| 4 | 0-9 | 0-16 | 10-19 |
|   |     |      | 39-55 |
| 5 | 0-9 | 0-19 | 20-29 |
|   |     |      | 36-55 |
| 6 | 0-9 | 0-6  | 20-29 |
|   |     |      | 49-55 |
| 7 | 0-9 | 0-9  | 30-39 |
|   |     |      | 46-55 |

Referring particularly to FIG. 5A, each coincidence circuit ASIC 105 includes a set of row input shift registers 117 that receive the serial input data shifted into the circuit from up to twenty-two pairs of leads in the bus 103. Each shift register 117 is ten bits in length, and at the completion of a 250 nanosecond sample period, each pair of them hold the entire event data packet from a detector module. Similarly, a set of column input shift registers 118 connect to ten pairs of leads in the bus 103 to receive event data packets from detector modules that are to be compared for coincidence with the detector modules connected to the row input registers 117. As with the row input shift registers 117, the column input shift registers 118 are filled with data during the ten clock pulses of a sample period.

On the first clock pulse (C$_o$) of the next sample period, each event data packet in the input shift registers 117 and 118 are transferred in parallel to a set of 20-bit row holding registers 119 and 20-bit column holding registers 120. As shown in more detail in FIG. 5B, a multiplexer 121 connects each input shift register 117 or 118 to its respective holding register 119 or 120, and it selects the input register for loading into the holding register during the first clock pulse (C$_o$) of the sample period. During the remaining nine clock pulses of each sample period, a second input to each multiplexer 121 is selected for loading into the holding registers 119 and 120. The ten column holding registers 120 are cascade connected through the second input of their associated multiplexer 121 and the twenty-two row holding registers 119 are similarly connected through their associated multiplexers 121 to the next lowest holding register 119 in the chain. On each of the subsequent nine clock pulses (C$_1$-C$_9$) in the sample period, therefore, the contents of each holding register 119 and 120 are transferred in parallel to the next lowest holding register in the chain. In other words, the contents of the row holding registers 119 are shifted to the next register in the chain (upward in FIG. 5A), and the contents of the column holding registers 120 are shifted to the next register in their chain (left in FIG. 5A).

It is through this transfer of event data packets in the chains of row and column holding registers that the 250 nanosecond sample period is divided into ten 25 nanosecond time increments. During each of these time increments, the event data packet in the first column holding register 120 is simultaneously compared with the thirteen event data packets in the first thirteen row holding registers 119 by thirteen comparator circuits 115. One hundred and thirty comparisons are therefore made for coincidence by a single coincidence circuit 105 during a single sample period. By time multiplexing ten sets of thirteen comparisons during each sample period, the comparison hardware is reduced in complexity and cost by a factor of ten.

Referring still to FIG. 5A, the comparison of the event data packets for coincidence events is performed by a set of thirteen comparator circuits 115. Each comparator circuit 115 connects to receive the 20-bit event data packet currently stored in the first column holding register 120 and compare it with the 20-bit event data packet currently stored in a respective one of the first thirteen column holding registers 119. The comparator circuits 115 are configured and operated by configuration and control registers 116, which is coupled to the configure logic 113 (FIG. 4) through a bus 122. As will be explained below, during each 25 nanosecond time increment, each comparator circuit 115 makes the comparison and produces a 36-bit output packet which is latched in an output holding register 125 and which is subsequently inserted in a chain of thirteen, cascade connected output registers 26. One bit in this output packet indicates whether a coincidence event was detected.

Referring to FIGS. 5A and 5C, the output registers 126 are chained together by multiplexers 127 which receive at one of their inputs the 36-bit output packet from a respective one of the holding registers 125, and which receive at their second input the 36-bit output packet stored in the previous output register 126 in the chain. The coincidence indicating bit in the latter output packet is applied through a line 128 to the select terminal on the multiplexer 127. As a result, during each 25 nanosecond time increment, one of the two output data packets will be coupled through the multiplexer 127 and stored in the output register 126. If the output data packet in the previous register 126 indicates a coincidence, that data packet will be passed on to the next output register 126 in the chain. Otherwise, the 36-bit output packet from the associated holding register 125 is loaded in the output register 126.

The output register chains in all seven ASICs 105 are connected to form one long output register chain. The 36-bit output of the last output register 126 in this chain is applied to the coincidence registers 106 (FIG. 4). While the 36-bit output packets appear at the output of the chain at a 40 MHz rate, only those which indicate coincidence are stored in the coincidence registers 106 and sent to the sorter 34 as a 32-bit coincidence data packet (Table B).

Figure 6:
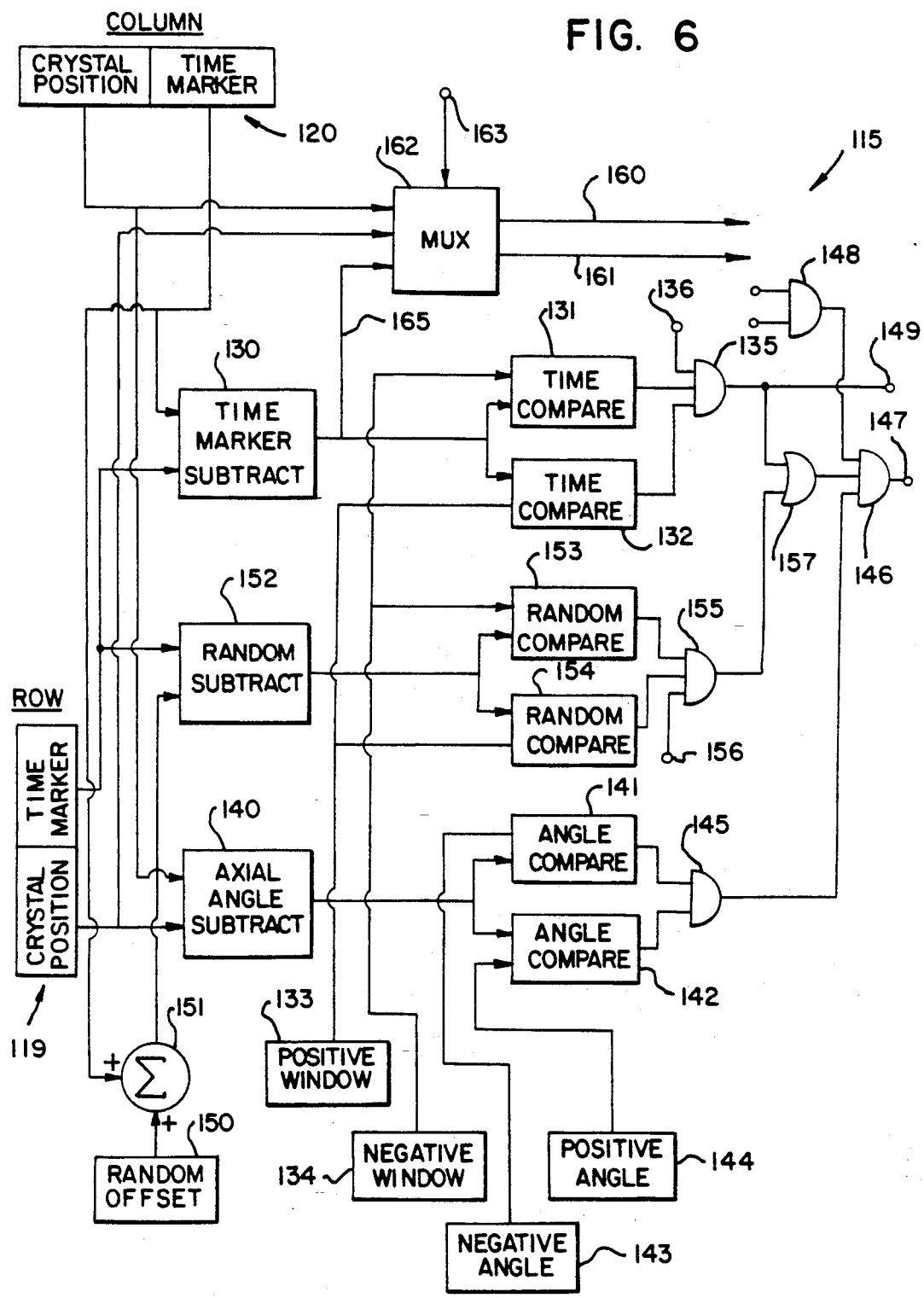
FIG. 6 is a circuit diagram of a comparator circuit which forms part of the coincidence circuit of FIG. 5A.

Each comparator circuit 115 performs a number of functions during a 25 nanosecond time increment on the two event data packets applied to its inputs. Referring to FIG. 6, each comparator circuit 115 includes a time marker subtracter 130 which receives the time markers from the event data packets in the respective holding registers 119 and 120 and produces a binary difference which is applied to one input on each of two time comparators 131 and 132. The binary difference indicates the time interval between the scintillation events detected in the two event data packets, and this time interval is compared with a preset coincidence window. The coincidence window is configured by loading a time interval into a positive window register 133 and loading a separate time interval into a negative window register 134. This can be accomplished by the operator from the console 15. Typically, these intervals are the same and in the preferred embodiment, each is set to 12.5 nanoseconds. The outputs of the comparators 131 and 132 are applied to an AND gate 135 along with a PROMPT ENABLE input 136, and if the two scintillation events are within either the positive or negative time window, coincidence is indicated at the output of AND gate 135. The control of the PROMPT ENABLE input 136 will be described in more detail below.

Even if time coincidence is detected, it will not necessarily be recognized if the BGO crystals which produced it are located in different axial planes. The z-axis location of the BGO crystal is indicated by five bits in the event data packet, and these bits are applied to the respective inputs of an axial angle subtracter 140. The binary difference signal is applied to the inputs of two angle comparators 141 and 142 which receive their other inputs from respective angle registers 143 and 144. The values in the angle registers 143 and 144 may be configured by the operator, and are typically set to a value of from 1 to 3. As a result, when the two scintillation events occur within the preset axial range, a logic high voltage is produced at an AND gate 145. On the other hand, the AND gate 145 remains low if the two detected events occurred in axial planes which are outside the preset range. The output of AND gate 145 thus serves as a filter signal which is combined with the time coincidence signal from AND gate 135 at an AND gate 146. A coincidence present signal is indicated at an output 147 when both conditions are true and both the ROW event present bit and COLUMN event present bit in the event data packet are set as indicated by an AND gate 148.

The comparator circuit 115 not only records coincidence events, but it also estimates random coincidence events which are employed during image reconstruction to reduce noise caused by random gamma rays. Referring still to FIG. 6, this is accomplished by adding a random offset interval to the time marker in the column holding register 120. This offset is configurable and is stored in a register 150 which serves as one input to a digital adder 151 that combines it with the time marker in holding register 119. The offset time marker from adder 151 is subtracted from the time marker in the row holding register 119 by a subtracter 152. The result is applied to two comparators 153 and 154 which receive at their other input the above-described coincidence window values from registers 133 and 134. If the offset time marker is within the preset coincidence windows and a DELAY EN control line 156 is set, the output of an AND gate 155 goes high and is applied to an OR gate 157. If the scintillation events are within the preset axial angle, as indicated by AND gate 145 and described above, AND gate 146 indicates a coincidence event. The output 149 of AND gate 135 indicates whether the coincidence event was produced by a true event or a random event.

Referring still to FIG. 6, in addition to producing an indication that a coincidence event has been detected, the comparator circuit 115 also produces the addresses, or positions, of the two BGO crystals that recorded the event at outputs 160 and 161. During normal operation, these are coupled through a multiplexer 162 directly from the row holding register 119 and column holding register 120. However, during a coincidence timing calibration mode indicated on a control line 163, the multiplexer 162 replaces the least significant position bits with the 6-bit output 165 of the time marker subtracter 130. Thus, each coincidence event packet will indicate the two detector modules that produced the event as well as the measured time interval between the detection of the two gamma rays. This time difference information may be used to calibrate the electronic circuits in the PET scanner system.

Figure 7:
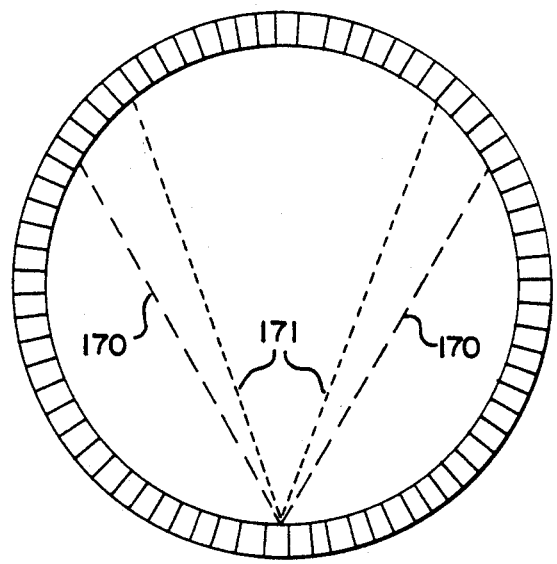
FIG. 7 is a pictoral view of the bore of the pet scanner system of FIG. 1 illustrating the different transaxial fields of view.

Referring to FIGS. 5A and 7, another aspect of the present invention is the ability to configure the transaxial field of view in which coincidence events will be detected. When all thirteen comparator circuits 115 are enabled during each of the ten 25 nanosecond time increments, the maximum transaxial field of view (TFOV) is examined for coincidence events. This is illustrated by dashed lines 170 in FIG. 7. However, this TFOV can be narrowed as shown by the dotted lines 171 by downloading ten mask words to the configuration and control circuit 116. Each mask word is operative during a respective one of the ten time increments and each contains thirteen bits which indicate whether the corresponding comparator circuit 115 is operative during that time increment. When thus disabled, of course, the comparator circuit 115 cannot recognize a coincidence event appearing at its inputs. The set of transaxial FOV mask words will differ for each of the ASICs 105, and they are downloaded through the VME backplane 31 and configure logic 113 as described above in connection with FIG. 4.

Figure 8:
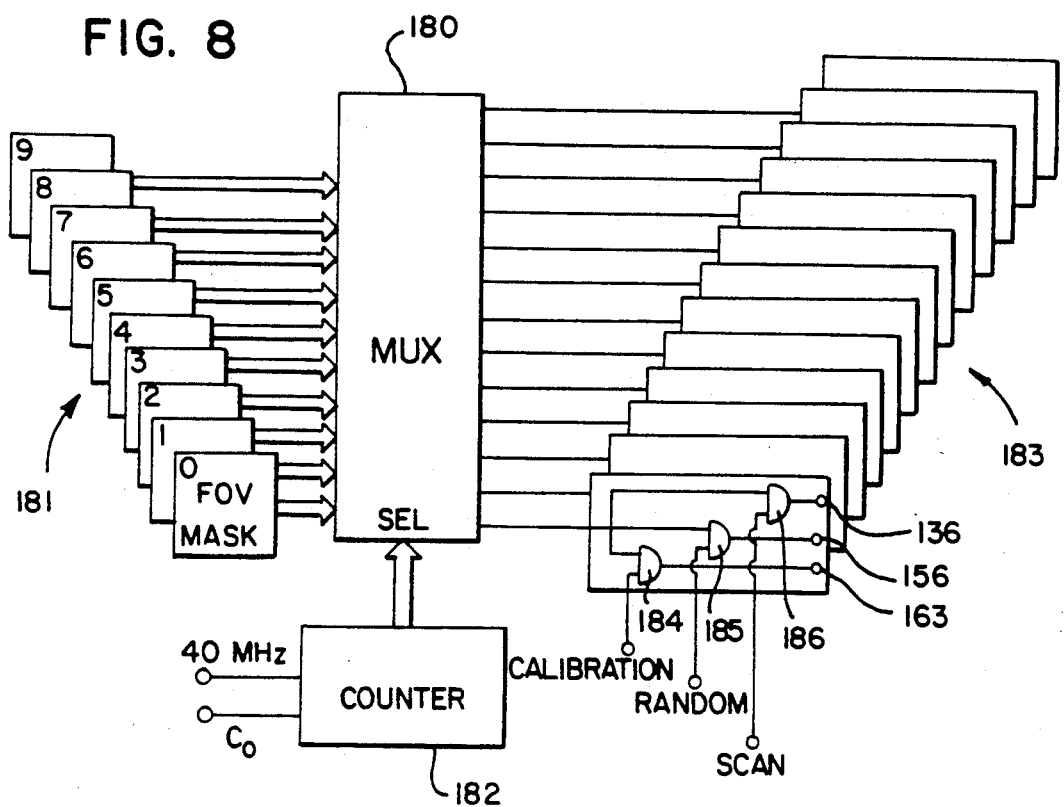
FIG. 8 is a circuit diagram of a field of view circuit which forms part of the coincidence circuit of FIG. 5A.

Referring particularly to FIG. 8, the circuit for controlling the transaxial field of view includes a ten channel multiplexer 180 which receives at each of its ten input channels one of the thirteen-bit field of view masks 181. The multiplexer 180 is responsive to a code produced by a counter 182 to select one of the thirteen-bit transaxial FOV masks and apply it to a set of thirteen comparator enable circuits 183. The counter 182 is driven by the 40 MHz clock and is reset at the beginning of each 250 nanosecond sample period by the clock pulse $C_0$. During each of the ten 25 nanosecond time increments a different successive one of the FOV masks 181 is selected by the counter 182 and multiplexer 180 and used to determine which comparators are enabled.

Each comparator enabling circuit 183 is comprised of three AND gates 184-186 which receive at one of their inputs a TFOV mask bit. The gate 184 also receives a calibration enable signal which is set when the system is in the calibration timing mode. Its output drives the control line 163 which enables the MUX 162 (FIG. 6) in the comparator circuit 115. The AND gate 185 receives at its second input a RANDOM enable signal when random coincidences are to be recorded, and its output drives the control line 156 in the comparator circuit 115. And finally, the second input on the AND gate 186 is driven by a SCAN control line which indicates that a scan is in progress. Its output drives the control line 136 which connects to the AND gate 135 in the comparator circuit 115 (FIG. 6). The transaxial FOV mask therefore determines which of the thirteen comparator circuits 115 are enabled during each time increment of the 250 nanoseconds sample period, and thereby determines the transaxial field of view of the acquired data.

It can be appreciated by those skilled in the art that many variations are possible from the preferred embodiment described herein without departing from the spirit of the invention. By dividing the sample period into ten time increments, the preferred embodiment provides nearly a ten fold reduction in the number of coincidence detector channels. This number may be different and is a matter of engineering choice.

We claim:

1. A positron emission tomographic scanner which comprises:

detector means having a plurality of detector modules which produce a corresponding plurality of event data packets during a sample period, each event data packet indicating the location of the detector module which produced it and including a time marker indicative of the time at which a scintillation event was detected by the detector module;

a coincidence detector circuit connected to receive and store the plurality of event data packets produced during each sample period, the coincidence detector circuit including:

a) a comparator circuit coupled to receive the time markers in a pair of said stored event data packets and being operable to compare them and indicate a coincidence event if the difference between the two received time markers is within a preset time window;

b) output register means connected to the comparator circuit for storing a coincidence data packet that includes an indication that a coincidence event has taken place and the location data for the two detector modules that produced the event data packets which are responsible for the coincidence event;

c) clock means for dividing each sample period into a plurality of time increments;

d) shift means connected to the clock means for changing the pair of stored event data packets coupled to the comparator circuits during each time increment, such that a plurality of pairs of event data packets are compared for coincidence events by the comparator circuit during each sample period; and image reconstruction means connected to the coincidence detector circuit for receiving the coincidence data packets therefrom and reconstructing an image.

2. The positron emission tomographic scanner as recited in claim 1 in which the coincidence detector circuit includes a plurality of comparator circuits and the shift means changes the pairs of stored event data packets coupled to each of said plurality of comparator circuits a plurality of times during each sample period.

3. The positron emission tomographic scanner as recited in claim 1 in which the shift means includes a set of cascade connected row holding registers, which each store respective ones of the event data packets, and a set of cascade connected column holding registers, which each store other respective ones of the event data packets, and one of the row holding registers and one of the column holding registers are coupled to the comparator circuit, wherein the location of the event data packets stored in the row holding registers and the column holding registers are changed during each time increment of the sample period.

4. The positron emission tomographic scanner as recited in claim 3 in which the coincidence detector circuit includes a plurality of comparator circuits, each of said comparator circuits being connected to respective ones of the row holding registers and to said one column holding register.

5. The positron emission tomographic scanner as recited in claim 4 which includes a plurality of output register means, each connected to a respective one of said plurality of comparator circuits.

6. The positron emission tomographic scanner as recited in claim 5 in which the plurality of output registers are cascade connected and the location of coincidence data packets stored therein are changed during each time increment of the sample period.

7. The positron emission tomographic scanner as recited in claim 4 in which the coincidence detector circuit includes means responsive to a transaxial field of view mask to control the number of comparator circuits operable during each time increment.

8. The positron emission tomographic scanner as recited in claim 7 in which the transaxial field of view of the coincidence detector circuit may be changed by changing the data in the transaxial field of view mask.

9. The positron emission tomographic scanner as recited in claim 1 in which the coincidence detector circuit includes a window register which stores said preset time window, and the value of said preset time window may be changed by storing a different value in said window register.

10. The positron emission tomographic scanner as recited in claim 1 in which the detector modules are disposed in a ring around a central axis, the event data packets each include axial position data, and the comparator circuit includes axial angle filter means which inhibit the indication of said coincidence event if the difference between the axial position data in the two event data packets being compared exceed a preset amount.

11. The positron emission tomographic scanner as recited in claim 10 in which the coincidence detector circuit includes an angle register which stores said preset amount, and the value of said preset amount may be changed by storing a different value in said angle register.

12. The positron emission tomographic scanner as recited in claim 1 in which the comparator circuit includes means for adding an offset to one of the time markers in each pair of stored event data packets and means for comparing the resulting pair of time markers and indicating a random coincidence event if the difference between these resulting pair of time markers is within a preset time window.

13. The positron emission tomographic scanner as recited in claim 12 in which the coincidence data packet stored by the output register means indicates when a random coincidence event is detected.

14. The positron emission tomographic scanner as recited in claim 1 in which the comparator circuit includes means responsive to a calibration mode signal for outputting said difference between the two received time markers, and the coincidence data packet stored by the output register means indicates said difference between the two received time markers.

* * * * *